(12) United States Patent
Joslyn

(10) Patent No.: US 6,605,159 B2
(45) Date of Patent: Aug. 12, 2003

(54) DEVICE AND METHOD FOR COLLECTING AND MEASURING CHEMICAL SAMPLES ON PAD SURFACE IN CMP

(75) Inventor: Michael J. Joslyn, Meridian, ID (US)

(73) Assignee: Micron Technology, Inc., Boise, ID (US)

(*) Notice: Subject to any disclaimer, the term of this patent is extended or adjusted under 35 U.S.C. 154(b) by 65 days.

(21) Appl. No.: 09/945,013

(22) Filed: Aug. 30, 2001

(65) Prior Publication Data

US 2003/0041882 A1 Mar. 6, 2003

(51) Int. Cl.⁷ .............................. B08B 7/04; B08B 3/04
(52) U.S. Cl. ..................... 134/18; 134/57 R; 438/692; 422/68.1; 451/8
(58) Field of Search ................. 436/5, 55; 422/62, 422/68.1, 99, 100, 101, 102, 105, 116, 81; 134/18, 6, 57 R; 451/8, 5, 6, 4, 56, 288, 290, 397; 438/690, 691, 692, 693, 14; 216/84, 88

(56) References Cited

U.S. PATENT DOCUMENTS

| | | | | |
|---|---|---|---|---|
| 5,384,986 A | * | 1/1995 | Hirose et al. | 451/444 |
| 5,536,202 A | * | 7/1996 | Appel et al. | 451/285 |
| 5,578,529 A | * | 11/1996 | Mullins | 438/692 |
| 5,595,527 A | * | 1/1997 | Appel et al. | 451/28 |
| 5,597,443 A | * | 1/1997 | Hempel | 438/693 |
| 5,683,289 A | * | 11/1997 | Hempel, Jr. | 451/56 |
| 5,934,974 A | * | 8/1999 | Tzeng | 451/6 |
| 5,944,590 A | * | 8/1999 | Isobe et al. | 451/288 |
| 6,045,434 A | * | 4/2000 | Fisher et al. | 451/6 |
| 6,190,236 B1 | * | 2/2001 | Drill | 451/41 |
| 6,241,587 B1 | * | 6/2001 | Drill et al. | 451/56 |
| 6,244,944 B1 | * | 6/2001 | Elledge | 451/296 |
| 6,283,840 B1 | * | 9/2001 | Huey | 451/288 |
| 6,293,139 B1 | * | 9/2001 | Keller et al. | 73/105 |
| 6,302,766 B1 | * | 10/2001 | Sethuraman et al. | 451/41 |
| 6,309,433 B1 | * | 10/2001 | Kinoshita | 51/307 |
| 6,331,139 B2 | * | 12/2001 | Walker et al. | 451/490 |
| 6,464,824 B1 | * | 10/2002 | Hofmann et al. | 156/345.16 |
| 6,481,446 B2 | * | 11/2002 | Yang et al. | 134/102.2 |
| 6,518,188 B2 | * | 2/2003 | Cook et al. | 438/692 |
| 2002/0048957 A1 | * | 4/2002 | Yang et al. | 438/692 |
| 2002/0173223 A1 | * | 11/2002 | Gitis et al. | 451/5 |
| 2003/0041882 A1 | * | 3/2003 | Joslyn | 134/18 |

\* cited by examiner

Primary Examiner—Alexander Markoff
(74) Attorney, Agent, or Firm—Knobbe, Martens, Olson & Bear, LLP

(57) ABSTRACT

A chemical collection assembly and a method for using the assembly such that a chemical-mechanical polishing (CMP) pad used in the manufacture of semiconductor wafers can be assessed for cleanliness. The method involves delivering solvent from the assembly's reservoir to an enclosed volume over the CMP pad. The solvent then brings contaminants imbedded on the CMP pad into solution. This solution is then drawn back up from the enclosed volume wherefrom a sample of the solution can be taken. That sample is then analyzed for the level of contaminants present therein, and the analysis is compared to a pre-determined level of cleanliness to determine whether the CMP pad should or should not continue to be used for semiconductor wafer manufacturing.

28 Claims, 6 Drawing Sheets

DEVICE AND METHOD FOR COLLECTING AND MEASURING CHEMICAL SAMPLES ON PAD SURFACE IN CMP

BACKGROUND OF THE INVENTION

1. Field of the Invention

The present invention relates to semiconductor processing and, in particular, concerns a method of conditioning and measuring pads used in planarizing surfaces of a wafer using chemical-mechanical polishing.

2. Description of the Related Art

Chemical-mechanical polishing (CMP) is a technique whereby surfaces are planarized by the simultaneous application of both an etching and a polishing process. Semiconductor wafers are often globally planarized using CMP processing. In a typical CMP process, the semiconductor wafer is placed on a carriage, and a pad is positioned over the wafer to contact the upper surface of the semiconductor wafer. The carriage and the pad are further rotated in opposite directions, and a slurry containing an etchant and abrasive particles flows between the upper surface of the semiconductor wafer and the pad. The combination of the mechanical polishing of the pad and the chemical etching action involved in this process serves to remove exposed surfaces of the wafer thereby planarizing the upper surface of the semiconductor wafer.

In one implementation, the CMP process is used for demascene processing in which excess layers of copper compounds are removed from the semiconductor wafer surface, leaving only the necessary copper conduit. After a time, newly removed copper compounds, such as $Cu(OH)_2$ and $Cu(OH)$, clog and contaminate the CMP pad, thereby degrading its planarization effectiveness. More specifically, as the CMP pad is used, contaminants build up within the pores or grooves of the CMP pad, thereby inhibiting an even distribution of slurry. This could cause uneven planarization of the wafer and necessary wafer materials might be removed.

To address these problems, methods have been developed to determine the level of contaminants on the CMP pad so as to indicate when the pad is no longer acceptable for use. One such method involves pouring a solvent, such as a solution of 1% nitric acid ($HNO_3$), onto the pad whereby the solvent draws the contaminants from the pad. Then, a sample of this solvent and contaminant mixture is taken from the pad using a pipette, and this sample is tested for the level of contaminants present in the solution using spectrometer technology, such as ion coupled plasma analysis.

This method has several problems. For example, pouring the solution on the pad in an uncontrolled manner may actually wash away contaminants from the area that will ultimately serve as the collection point. As a result, the sample taken may not be a representative sample of the level of contaminants actually on the rest of the pad.

Also, as stated above, the contaminants often reside in the grooves and pores of the CMP pad, so in order to get samples of solvent that contain a representative amount of contaminants, the sample should be taken from within the grooves or pores. However, the pipette tips are generally too large to fit down into the narrow grooves on the CMP pad. As a result, the sample taken may be inaccurate, and the user will likely make an inappropriate assessment of the CMP pad cleanliness. Another problem is that the solvent may absorb into the CMP pad after it is poured. As a result, it may be difficult to collect the required amount of solvent for testing.

Hence from the foregoing, it will be appreciated that there is a need for a device and method that will simply and accurately measure the amounts of contaminants deposited on a CMP pad in order to determine its level of cleanliness.

SUMMARY OF THE INVENTION

The present invention satisfies the aforementioned needs. The disclosed method and apparatus permit easier, more accurate, and more controlled sampling of the contaminants on a CMP pad.

One aspect of the present invention comprises a method of determining the cleanliness of a CMP pad. First, the user selects a solution that will dissolve contaminants on the CMP pad. Then, the user positions a retaining structure on a first surface of the CMP pad so as to define a controlled space and injects a controlled volume of solution onto the CMP within the controlled space. Next, the solution with dissolved contaminants is extracted from the controlled space adjacent the CMP pad. Finally, the extracted solution is sampled to determine the quantity of dissolved contaminants in the CMP pad, and it is determined, based on this sampling of the extracted solution, whether the CMP pad meets a pre-selected cleanliness threshold.

Another aspect of the present invention is an assembly for obtaining a sample indicative of the cleanliness of a CMP pad having a first surface. The assembly comprises a retaining structure that is positionable adjacent the first surface so as to define an enclosed volume adjacent the first surface of the CMP pad. The assembly also comprises a reservoir containing a sampling solution and a delivery mechanism for delivering the sampling solution to the enclosed volume such that the sampling solution absorbs contaminants on the first surface of the CMP pad. Furthermore, the assembly comprises an extraction mechanism that extracts the sampling solution from the enclosed volume such that the extracted sampling solution contains contaminants of the first surface of the CMP pad. The sampling solution can then be evaluated to determine the cleanliness of the first surface of the CMP pad.

Most of the solution will remain inside the enclosed space in the retaining structure after it is injected therein. Advantageously, the solution is easy to collect for subsequent sampling. Also, the enlarged area of the enclosed space allows sampling of contaminants that may be present in multiple grooves, where there may be different levels of contaminants. As a result, the present invention advantageously allows the user to take a more representative sample of the level of contaminants present on the CMP pad.

Another aspect of the present invention comprises a retaining structure that is adapted to be positioned adjacent a surface of the CMP pad, and the retaining structure defines an enclosed volume that retains fluid within the enclosed volume adjacent the surface of the pad. In this embodiment, a pipette is used to inject cleaning solution onto the surface of the CMP pad within the enclosed volume. The pipette is also used to extract cleaning solution from the enclosed volume for subsequent analysis. The analysis determines the level of contaminants to thereby ascertain whether the CMP pad is suitable for continued use. Advantageously, use of this embodiment of the chemical collection assembly allows for easy set up and break down because the components involved are preferably light and portable.

A different aspect of the present invention comprises a delivery system for delivering cleaning solution to the surface of the CMP pad. This embodiment also comprises a retaining structure that is positionable with respect to the surface of the CMP pad so as to define an area on the surface of the CMP pad into which the delivery system positions the cleaning solution. Additionally, a recovery system that recovers cleaning solution from the area on the CMP pad is used. A controller sends signals to the delivery system and the recovery system so as to induce delivery and recovery of the cleaning solution.

Advantageously, use of this embodiment of the present invention allows for easy assessment of the CMP pad cleanliness because it is substantially automated. Also, the correlation between pad use and pad cleanliness can be discerned more quickly and with more confidence because human error is unlikely to affect the data collected from the cleanliness testing.

These and other objects and advantages of the present invention will become more apparent from the following description taken in conjunction with the accompanying drawings.

DETAILED DESCRIPTION OF THE PREFERRED EMBODIMENT

Figure 1A:
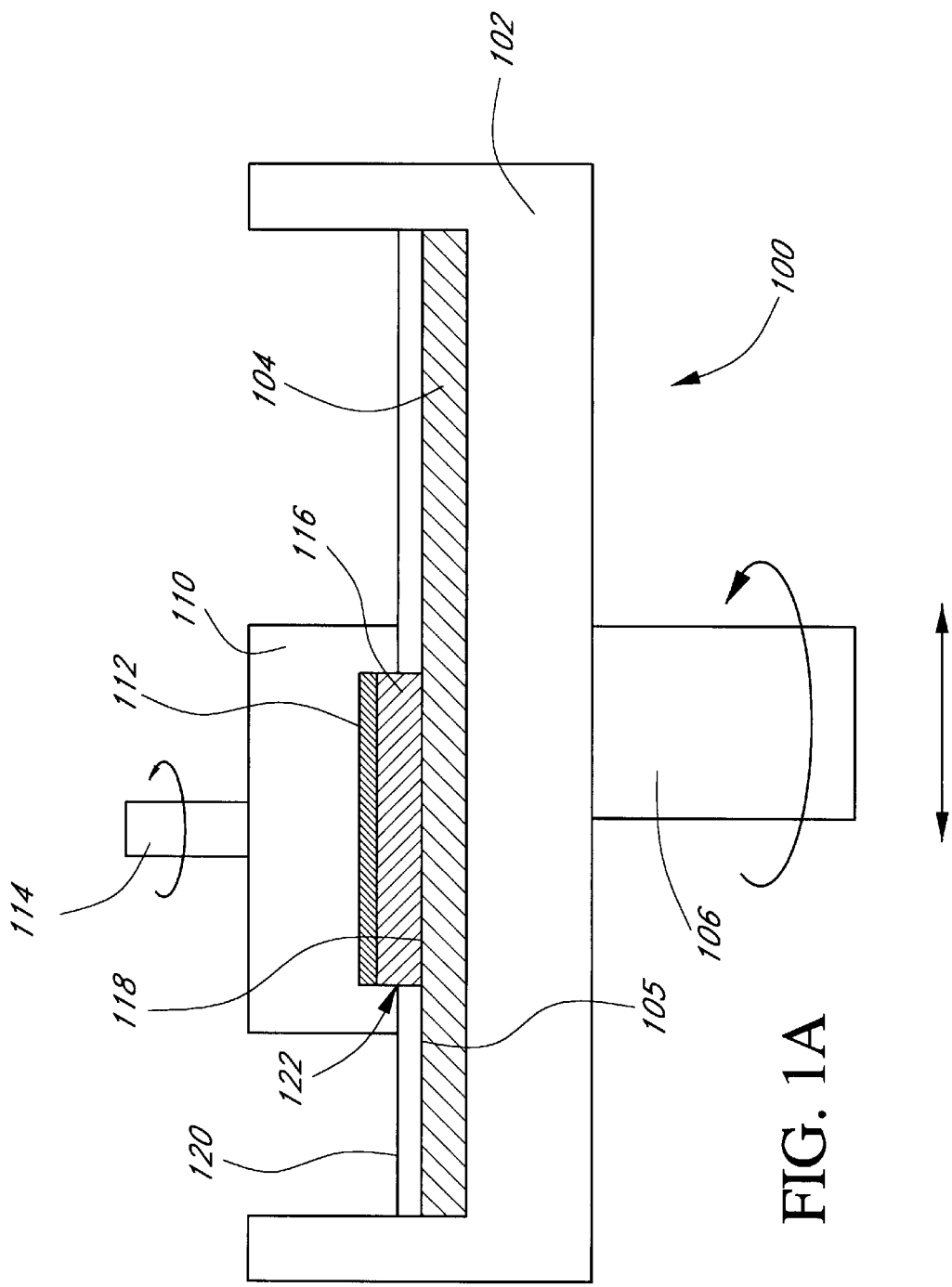
FIG. 1 is a schematic illustration representing one embodiment of a chemical-mechanical polishing (CMP) system.

Reference will now be made to the drawings wherein like numerals refer to like parts throughout. Referring initially to FIG. 1, an exemplary CMP system 100 is illustrated. In particular, the CMP system 100 includes a platen 102 that is rotated about a shaft 106 by a motor (not shown). The platen 102 retains a polishing pad 104, and the CMP system 100 also includes a carriage 110 that has a wafer receiving surface 112 which is adapted to retain a wafer 116 within the carriage 110. The carriage 110 is also adapted to be rotated about a shaft 114 by a motor (not shown).

The operation of the CMP system 100 is similar to the operation of similar CMP systems of the prior art. Basically, the platen 102 is rotated and the carriage 110 is rotated such that rotational movement between the silicon wafer 116 and the polishing pad 104 is imposed. The platen 102 and the carriage 110 are then moved together such that an exposed surface 118 of the wafer 116 is brought into contact with an outer surface 105 of the polishing pad 104. A wetting solution or slurry 120 is provided to the outer surface 105 of the polishing pad 104 so as to wet the interface 122 between the outer surface 105 of the polishing pad 104 and the exposed surface 118 of the wafer 116 to thereby enhance the polishing and removal of the surface 118 of the wafer 116. It will be appreciated that the CMP system 100 illustrated in FIG. 1 is simply exemplary of any of a number of well known CMP systems currently used in semiconductor fabrication and processing. The single platen 102 could be one of a number of platens in a more sophisticated system without departing from the spirit of the present invention.

As is understood in the art, the combined effects of the pad 104 frictionally engaging with the exposed surface 118 of the wafer 116 and the existence of etchants in the wetting solution or slurry 120 results in the systematic removal of layers of the exposed surface 118 of the wafer 116. As the layers of material are removed from the exposed surface 118 of the wafer 116, contaminants, such as $Cu(OH)_2$ or $Cu(OH)$ in demascene processing, deposit onto the outer surface 105 of the pad 104. As the CMP process continues, more and more material collects on this outer surface 105 and especially the grooves of the pad 104 thereby degrading the planarization properties of the pad 105. This problem is compounded if the pad 105 is used repeatedly for multiple wafers 116.

Figure 2:
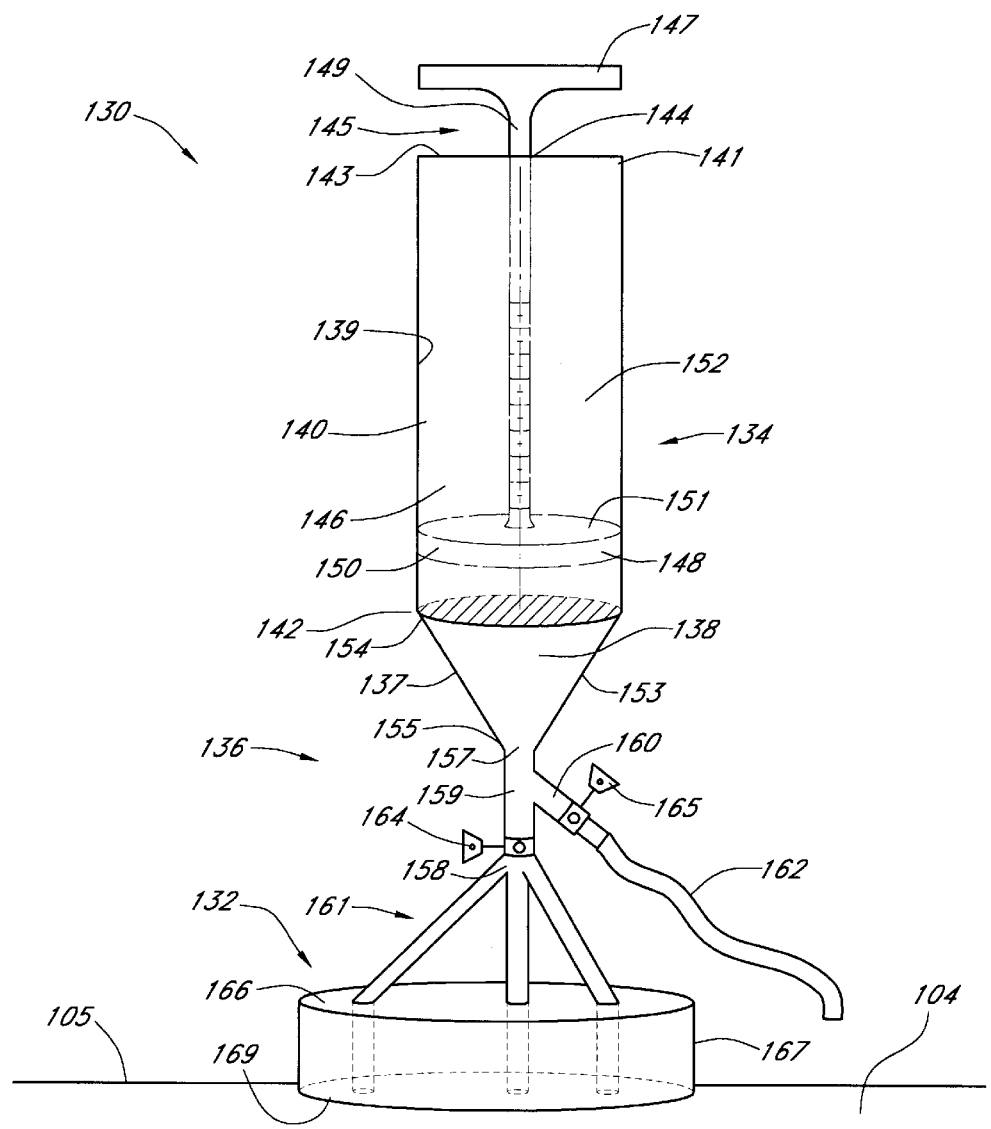
FIG. 2 is a perspective view of one embodiment of a chemical collection assembly of the present invention.

FIG. 2 illustrates one embodiment of a chemical collection assembly 130. As shown, the chemical collection assembly 130 generally comprises a reservoir 134, a stem section 136, and a retaining structure 132. As shown, the chemical collection assembly 130 is placed adjacent the exposed surface 105 of the CMP pad 104. The reservoir 134, the stem section 136, and the retaining structure 132 are hollow so that a solvent 138 can flow through them. The solvent 138 is preferably selected to dissolve contaminants present on the exposed surface 105 of the CMP pad 104. As will be discussed in greater detail below, the solvent 138 is injected from the reservoir 134 through the stem section 136 to the retaining structure 132 and vice versa in order to measure the cleanliness of the exposed surface 105 of the pad 104.

As shown in FIG. 2, one embodiment of the reservoir 134 comprises a cylinder 140 comprising a first end 141 and a second end 142. The reservoir 134 further comprises an inner surface 139 which defines a first volume 146. As will be described below, when the solvent 138 is in the reservoir 134 of the chemical collection assembly 130, the solvent 138 resides in the first volume 146. Furthermore, FIG. 2 shows that at the first end 141 of the cylinder 140 is a first surface 143, which substantially closes off the first end 141 of the cylinder 140 except for an aperture 144. Through the aperture 144 passes a plunger assembly 145.

FIG. 2 shows that the plunger assembly 145 comprises a plunger 148, which is cylindrically shaped and has an outer second surface 150. Preferably, the second surface 150 of the plunger 148 is positioned sufficiently close to the inner surface 139 of the reservoir 134 such that it creates a loose seal therebetween. At a third surface 151 of the plunger 148 is a shaft 149, which passes through the aperture 144 in the first surface 143 of the cylinder 140. Connected to the shaft 149 is a handle 147, both of which can take on a variety of shapes and sizes. As will be described below, the plunger assembly 145 functions in a manner such that when force is applied to the handle 147 in order to depress it, the force is transferred to the shaft 149 and ultimately to the plunger 148. As stated, the geometry of the plunger 148 preferably creates a seal between the plunger 148 and the inner surface 139 of the reservoir 134. This seal ensures that solvent 138 is forced from the cylinder 140 when the handle 147 is depressed, and solvent 138 is drawn up into the cylinder 140 when the handle 147 is lifted both due to vacuum suction.

FIG. 2 also illustrates that the reservoir 138 further comprises a funnel 153. The funnel comprises a large diameter first end 154 and a small diameter second end 155 with a wall 137 connecting both. More specifically, the first end 154 of the funnel 153 lies adjacent to the second end 142 of the cylinder 140. The funnel 153 acts to channel the solvent 138 from the cylinder 140 into the stem section 136.

As stated, the chemical collection assembly 130 also comprises the stem section 136. As shown in FIG. 2, the stem section 136 generally comprises a main shaft 159, a sampling shaft 160, and a plurality of delivery shafts 161. As will be described in greater detail below, the stem section 136 provides a means for delivering solvent 138 to and from the reservoir 134.

FIG. 2 further shows that the main shaft 159 has a first end 157 and a second end 158 wherein the first end 157 of the main shaft 159 lies adjacent to the second end 155 of the funnel 153. The second end 158 of the main shaft 159 splits off into the plurality of the delivery shafts 161. In the embodiment shown, there are three delivery shafts 161, and the axes of the delivery shafts 161 extend at an obtuse angle with respect to the axis of the main shaft 159, and the delivery shafts 161 extend to the retaining structure 132. Preferably, the individual delivery shafts 161 are evenly spaced around the main shaft 159. As will be described below, the use of a plurality of evenly-spaced delivery shafts 161 ensures that the solvent 138 will be applied evenly over a specified area of the CMP polishing pad 104.

Furthermore, according to the embodiment shown in FIG. 2, the sampling shaft 160 extends from a midpoint in the main shaft 159. Connected to the sampling shaft 160 is a flexible hose 162. As will be described in greater detail below, the sampling shaft 160 and flexible hose 162 allow samples of solvent 138 to be drawn from the chemical collection assembly 130 so as to measure the cleanliness of the CMP polishing pad 104.

Both the main shaft 159 and the sampling shaft 160 comprise a valve 164, 165 respectively. The valves 164, 165 are standard in the art, and as will be described below, the valves 164, 165 control the flow of solvent 138 through their respective shafts 159, 160 of the chemical collection assembly 130.

As stated, the chemical collection assembly 130 also comprises the retaining structure 132. In the embodiment shown in FIG. 2, the retaining structure 132 comprises a wall 167, which defines a first upper aperture 166 and a second lower aperture 169. In the embodiment shown, the retaining structure 132 comprises a ring shape. In one embodiment, the diameter of the retaining structure 132 is 1.5 to 2.0 inches.

As will be described in greater detail below, in order to evaluate the cleanliness of a polishing pad 104, the chemical collection assembly 130 is placed over the outer surface 105 of the polishing pad 104 such that a section of the outer surface 105 covers the second lower aperture 169 of the retaining structure 132. In this manner, the retaining structure 132 and CMP pad 104 combination defines a volume 152 wherein solvent 138 can dissolve contaminants located on the outer surface 105 of the pad 104. As will be discussed below, placement of the retaining structure 132 in this manner retains the majority of solvent 138 injected onto the surface 105 of the pad 104. Advantageously, collection of a sample of this solvent 138 with dissolved contaminants contained therein is facilitated because the solvent 138 will not run out from the volume 152 or excessively soak into the CMP pad 104.

Figure 3:
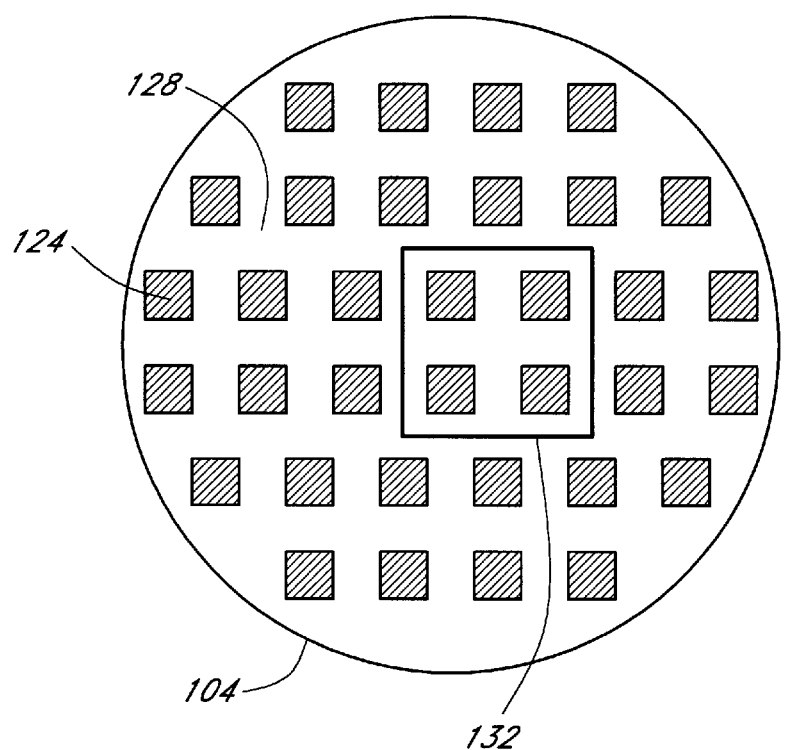
FIG. 3 is a top view of various embodiments of chemical retaining structures of the present invention.
Figure 3:
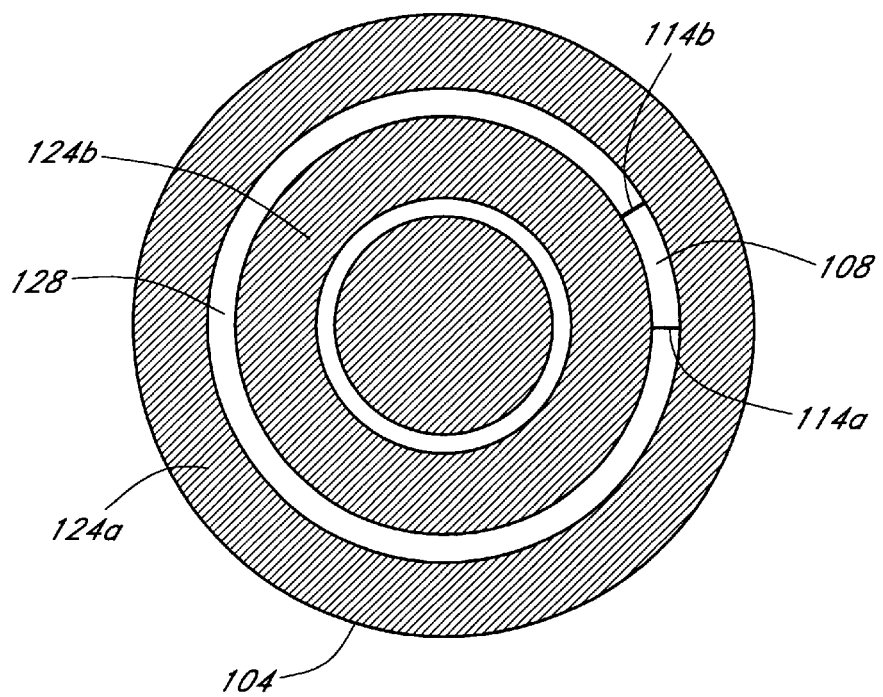

FIG. 3 illustrates different embodiments of the retaining structure 132 mounted atop a CMP pad 104. As shown, the retaining structure 132 can take on a variety of shapes and sizes depending upon the type of CMP pad 104 that is being tested. A CMP pad 104 often has a plurality of protrusions 124 with corresponding grooves 128 between the protrusions 124. One embodiment of the retaining chamber 132 is sized so as to lie substantially in the groove 128 and enclose a plurality of protrusions 124. The shape of the retaining structure 132 allows solvent 138 to flow over an enlarged area of the CMP pad 104 and coat a multitude of surfaces. Thus, samples taken from the retaining structure are more representative of the overall pad 104 cleanliness because different areas of the pad can contain different amounts of contaminants.

Another embodiment of the retaining chamber 132 comprises two walls 114a, 114b that are set substantially inside the groove 128 and extend between the nearby protrusions 124a, 124b so as to define a first volume 108. When solvent 138 is injected between the walls 114a, 114b, the solvent 138 is retained by the walls 114a, 114b and the protrusions 124a, 124b and pools within the first volume 108. Advantageously, this embodiment of the retaining structure 132 allows the user to target specific areas of the CMP pad 104 for testing without having to form several different retaining chamber 132 shapes.

Advantageously, the use of the retaining structure 132 defines an area in which the solution can be contained. As illustrated above, the retaining structure 132 can comprise an enclosed shape that is positioned on an exposed surface 105 of the CMP pad 104 or the retaining structure 132 can comprise a shape that is positionable within one of the grooves 128. Moreover, the retaining structure 132 can also be defined by a combination of structures, including protrusions on the pad 104 that result in an enclosed volume without departing from the spirit of the present invention.

Figure 4:
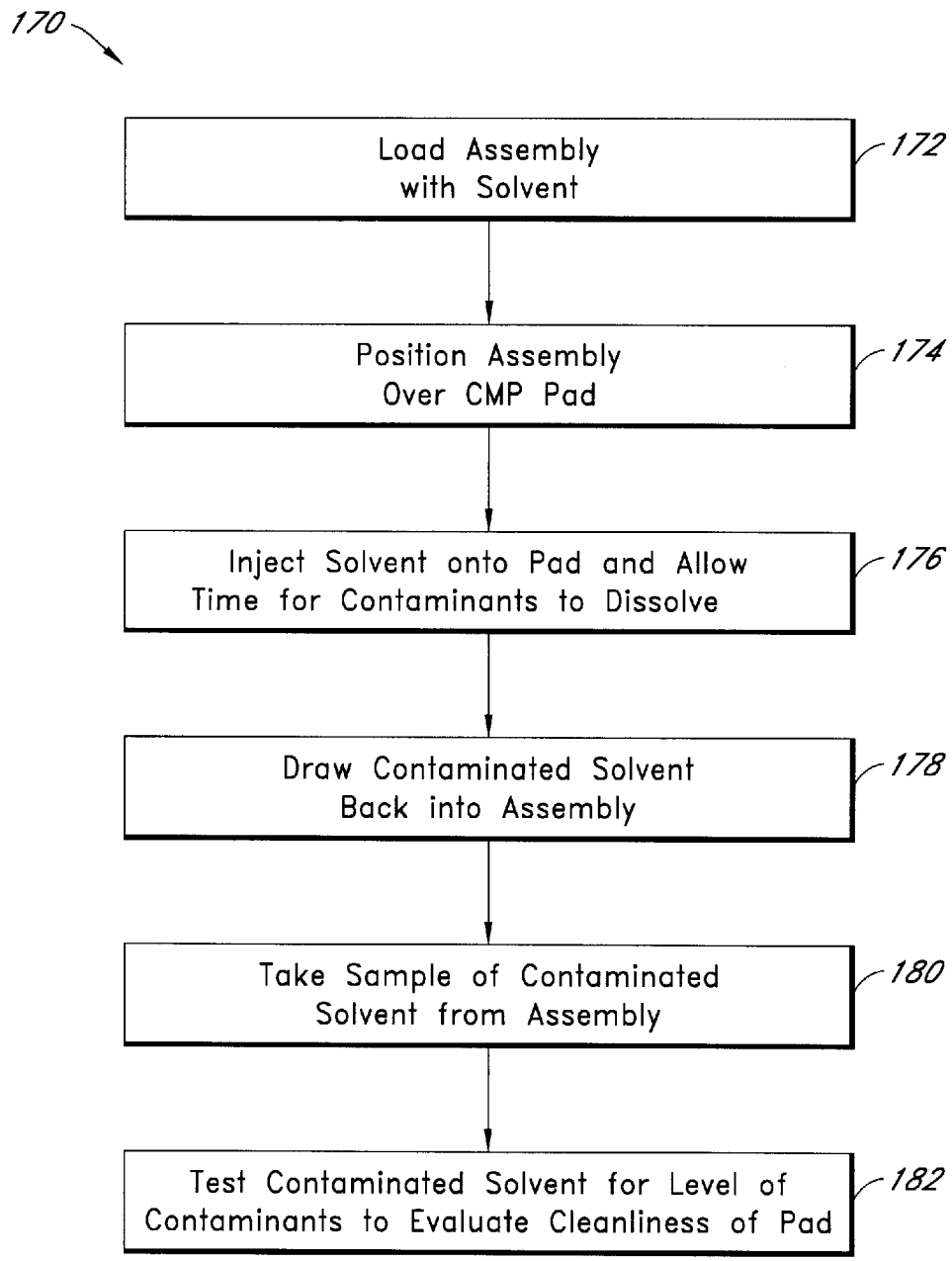
FIG. 4 is a flow chart illustrating the general process steps of the chemical collection and measurement method of the present invention.

FIG. 4 illustrates a method 170 of evaluating the cleanliness of a CMP pad 104 using a chemical collection assembly 130 similar to the assembly 130 shown in FIG. 2. As shown, a first step 172 of the method 170 involves loading the empty chemical collection assembly 130 with solvent 138. In one embodiment, this can be accomplished by first opening the valve 164 on the main shaft 159 and closing the valve 165 on the sampling shaft 160. Next, the handle 147 of the plunger assembly 145 is depressed toward the first end 141 of the cylinder 140 until the handle 147 stops. Then, the retaining structure 132 is positioned into a pool of solvent 138 such that the lower aperture 169 of the retaining structure 132 lies underneath the surface of the pool of solvent 138. Next, the handle 147 of the plunger assembly 145 is raised away from the first end 141 of the cylinder 140, and solvent is drawn into the chemical collection assembly 130. More specifically, the plunger 148 of the plunger assembly 145 is designed to create vacuum suction when the handle 147 is raised in this manner. Special attention is given during the first step 172 to ensure that the lower aperture 169 of the retaining structure 132 remains underneath the surface of the pool of solvent 138 such that the vacuum suction draws only solvent 138 and not air into the chemical collection assembly 130. The handle 147 is lifted until the desired amount of solvent 138 is drawn up into the chemical collection assembly 130. In one embodiment, the desired amount of solvent 138 for testing is approximately 300 milliliters.

At this point, as shown on FIG. 4, a second step 174 of the method 170 involves positioning the chemical collection assembly 130 over the exposed surface 105 of the CMP pad 104. More specifically, the chemical collection assembly 130 is positioned such that the wall 167 of the retaining structure 132 creates a seal between the retaining structure 132 and the exposed surface 105 of the CMP pad 104. As will be described below, the chemical collection assembly 130 is most effective when solvent 138 does not leak from the retaining structure 132 into the CMP pad 104.

FIG. 4 shows that a third step 176 of the method 170 entails injecting solvent 138 through the first upper aperture 166 and into the retaining structure 132 to thereby coat one area of the CMP pad 104. First, the valve 164 of the main shaft 159 is opened if it is not already. Then, the handle 147 of the plunger assembly 145 is depressed until a desired amount of solvent 138 is delivered into the retaining structure 132. As stated, depressing the handle 147 of the plunger assembly 145 forces the solvent 138 to flow from the reservoir 134 through the stem section 136 and into the retaining structure 132. Next, the solvent 138 dissolves and draws up contaminants from the exposed surface 105 of the CMP pad 104.

As stated above, the retaining structure 132 on top of the CMP pad 104 defines an enclosed volume 152 within which the solvent 138 dissolves contaminants present on the CMP pad 104. Preferably, the retaining structure 132 holds the majority of the solvent 138 within its wall 167. As such, the contaminants on the pad 104 will not be washed away from the retaining structure 132, and the level of contaminants in the sample of solvent 138 subsequently taken from the retaining structure 132 will be representative of the level of the contaminants that were on the pad 104 prior to testing. Advantageously, this allows for more accurate cleanliness testing.

As mentioned above, contaminants in the pad 104 often reside in the grooves of the CMP pad. It is understood that the amount of contaminants may vary along a single groove, and different grooves may have different amounts of contaminants contained therein. Due to the enlarged area of the second lower aperture 169 of the retaining structure 132, the solvent 138 can spread out over the CMP pad 104 and dissolve contaminants along the length of a groove and affect multiple grooves simultaneously. As a result, the sample of solvent 138 with contaminants contained therein is more likely to be an average measurement of contaminants contained on the CMP pad 104. Advantageously, this results in a more accurate assessment of the cleanliness of the entire CMP pad 104.

As shown on FIG. 4, the method 170 includes a fourth step 178. In this step 178, the solvent 138 is drawn back through the stem section 136 and into the reservoir 134. This is achieved by lifting the handle 147 of the plunger assembly 145 until a required amount of solvent 138 with dissolved contaminants is drawn into the stem section 136 and reservoir 134. The valve 164 on the main shaft 159 of the stem section 136 is then closed.

A fifth step 180 of the method 170 shown on FIG. 4 involves sampling the solvent 138 containing contaminants. First, the valve 165 on the sampling shaft 160 is opened, and then the handle 147 of the plunger assembly 145 is depressed. This causes solvent 138 with contaminants dissolved therein to move from the reservoir 134 through the stem section 138 and then out the sampling shaft 160 and into a sampling receptacle (not shown). The handle 147 of the plunger assembly 145 is depressed until a required amount of solvent 138 with contaminants dissolved therein is delivered into the sampling receptacle. In one embodiment, an adequate amount of sample is approximately five to ten milliliters.

The solvent 138 with contaminants dissolved therein is then moved to testing equipment in a sixth and final step 182 of the method 170 as shown in FIG. 4. Testing preferably involves using equipment known in the art to test the presence of substances in liquid media. In one embodiment, spectrometer technology, such as ion coupled plasma analysis, is used to measure the amount of contaminants. The results from the testing equipment can be compared to a pre-selected level of CMP pad 104 cleanliness in order to determine whether the CMP pad 104 should be used further, cleaned and re-conditioned with a diamond wheel, or discarded.

Advantageously, this method 170 allows for easy collection of the solvent 138 because the solvent 138 is pooled within the retaining chamber 132, allowing the delivery shafts 161 to simply draw up solvent 138 therefrom with vacuum suction. Also, the enlarged area of the retaining structure 132 allows for sampling of contaminants that may be present across a single or multiple grooves. As a result, the method 170 allows the user to take a more representative sample of the level of contaminants present on the CMP pad because different locations on the pad 104 might contain different levels of contaminants. Finally, frequent and repeated utilization of this method 170 will likely lead to an increased understanding of the correlation between CMP pad use and cleanliness because testing data can be compiled and studied. Advantageously, the CMP process will likely become more efficient because the user will have a good approximation as to when the CMP pad 104 is too contaminated for further use.

Figure 5:
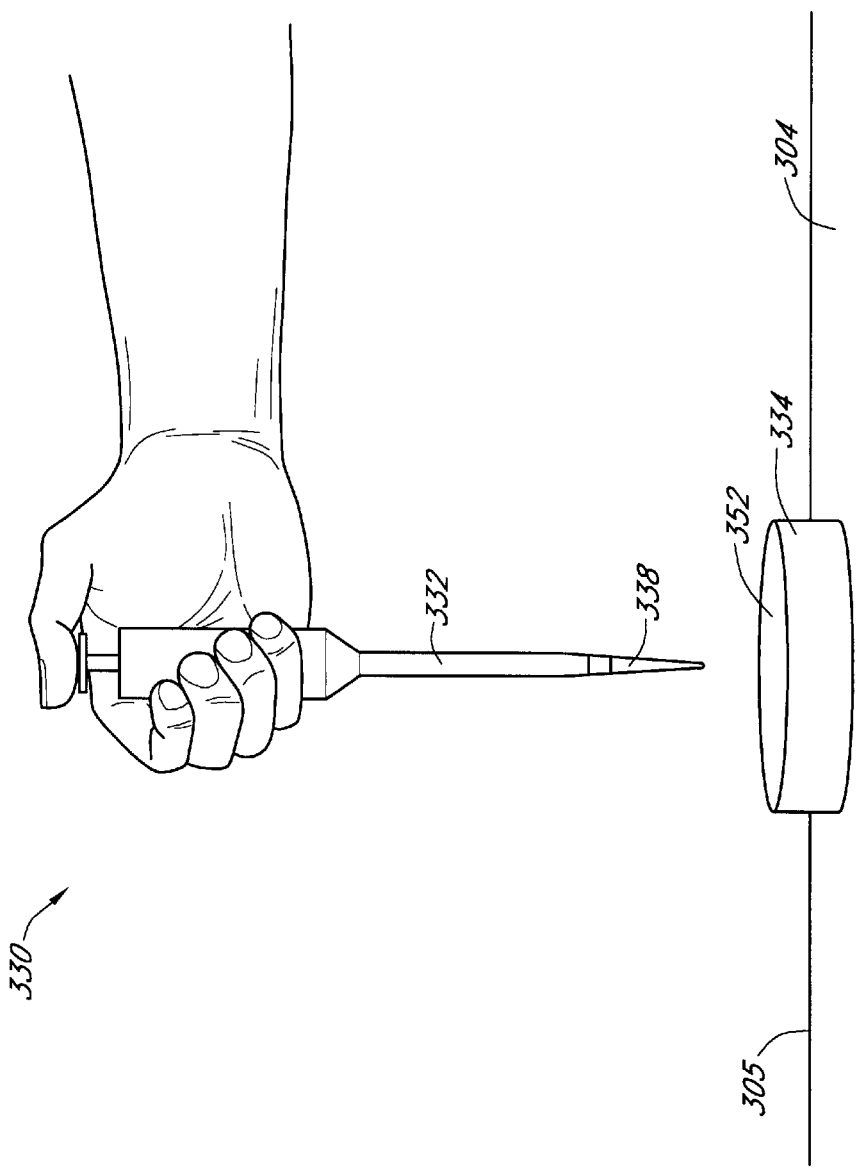
FIG. 5 is a perspective view of another embodiment of the chemical collection assembly of the present invention.

FIG. 5 illustrates another embodiment of a chemical collection assembly 330. As shown the chemical collection assembly 330 comprises a pipette 332, and a retaining structure 334. The pipette 332 is an instrument well known in the art used for injecting fluid to a desired location or sucking up fluid therefrom. The retaining structure 334 is similar to the retaining structure 134 described above, and as shown, the retaining structure 334 is placed atop an exposed surface 305 of a CMP pad 304. Similar to the chemical collection assembly 130 described above, testing the CMP pad 304 cleanliness involves positioning the retaining structure 334 over the CMP pad 304 in order to define a volume 352 into which a solvent 338 can be introduced and substantially retained. Upon introduction into the volume 352, the solvent 338 dissolves contaminants located on the CMP pad 104. Then, the pipette 332 is used to draw solvent 338 with dissolved contaminants from the retaining structure 334 for subsequent testing. Advantageously, a user of this embodiment of the chemical collection assembly 330 can easily set up and remove the necessary equipment because the pipette 332 and retaining structure 334 are easily portable.

Figure 6:
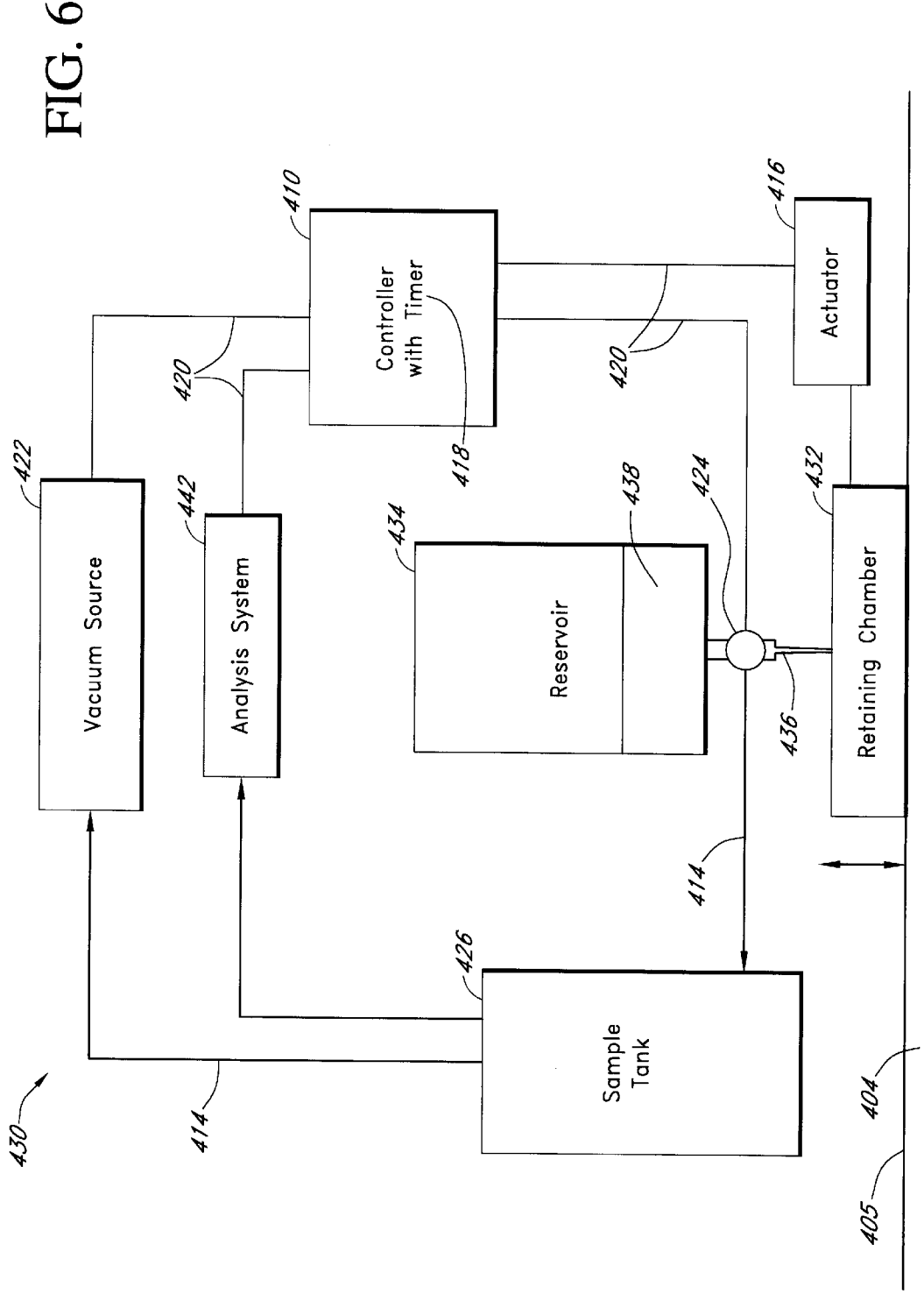
FIG. 6 is a schematic view of another embodiment of the chemical collection assembly of the present invention.

FIG. 6 illustrates a substantially automated embodiment of the chemical collection assembly 430. As shown, the chemical collection assembly 430 comprises a reservoir 434, a stem section 436, and a retaining structure 432, all of which are substantially similar to the reservoir 134, the stem section 136, and the retaining structure 132 described above. As shown, the stem section 436 also comprises a controllable valve 424, which controls the flow of solvent 438 through the stem section 436. Also, the chemical collection assembly 430 comprises a sample tank 426, which in one embodiment, comprises a cylindrical shape. The reservoir 434 holds a solvent 438, and as will be described in more detail below, the solvent 438 is delivered to and from the retaining structure 432 or to the sample tank 426 through the stem section 436 with the aid of a variety of components.

The chemical collection assembly 430 also comprises a vacuum source 422, used to generate a suction force. As shown in FIG. 6, the vacuum 422 is connected to the sample tank 426 by way of a vacuum hose 414. As will be described in greater detail below, the vacuum source 422 forces the solvent 438 to move through the chemical collection assembly 430.

FIG. 6 also illustrates that the chemical collection assembly 430 can include an actuator 416 that is connected to the retaining structure 432 in order to move the retaining structure 432 onto and off of an exposed surface 405 of a CMP pad 404. This operation will be described in greater detail below.

The chemical collection assembly 430 also comprises a controller 410 that is equipped with a timer 418 that regulates when control signals are sent, and the controller 410 regulates where the control signals are sent. As shown, the controller 410 is connected to the vacuum source 422, the actuator 416, and the valve 424 by way of signal lines 420. At desired time intervals determined by the timer 418, the controller 410 sends control signals to individually control the vacuum source 422, the valve 424, and the actuator 416 as will be described in greater detail below.

When cleanliness of the CMP pad 404 needs evaluating, the controller 410 sends a control signal to the actuator 416. The control signal is translated into movement of the actuator 416, which moves the retaining structure 432 onto the surface 405 of the CMP pad 404. Then, the controller 410 sends a signal to the valve 424, which opens the valve 424 into a first position such that solvent 438 flows from the reservoir 434 to the retaining structure 432 through the stem section 436. The controller 410 sends a signal to close the valve 424 when the desired amount of solvent 438 is delivered to the retaining structure 432. Next, the controller 410 sends a signal to shift the valve 424 into a second position such that solvent can flow from the retaining structure 432 to the sample tank 426 through the stem section 436. After a predetermined period of time, the controller 410 sends a signal to turn on the vacuum source 422, and the resulting vacuum pressure in the vacuum hose 414 causes solvent 438 to be drawn from the retaining structure 432 to the sample tank 424. Solvent 438 is then obtained from the sample tank 424 for subsequent testing in an analysis system 442 such as ion plasma analysis equipment.

In one embodiment, the solvent 438 in the sample tank 424 is automatically directed to the analysis system 442. After solvent 438 is delivered into the sample tank 424, the controller 410 sends a signal to turn on the vacuum source 422, thereby moving solvent 438 from the sample tank 424 into the analysis system 442. If the level of contaminants in the solvent 438 is too high, then the analysis system 442 sends a signal to the controller 410. In one embodiment, this signal turns on an audible alarm which notifies the user that the CMP pad 404 can no longer be used in its current condition.

Less human interaction is necessary when using the chemical collection assembly 430 because of the automation described above. The controller 410 will control, with a high degree of accuracy, the amount of solvent 438 delivered into the retaining structure 432 and the time interval between delivery to and delivery from the retaining structure 432. Advantageously, it is easy to assess the cleanliness of the pad 404 because the chemical collection assembly 430 requires lesser human interaction.

Also, it is understood that significant amounts of data will be generated from such testing. Test data would likely include the amount of time the pad was used, the visual appearance of the pad, and the amount of contaminants contained in the solvent. Collection of such data, after time would reveal the correlation between pad cleanliness, processing time, and pad appearance. Discovery of these correlations would eventually allow the user to run the CMP process more efficiently. This automated system, reduces the effect that human error would have on such test data. Advantageously, the user would be able to discern such correlations more quickly.

In one embodiment, the entire chemical collection assembly 430 is compact enough to be attached to a single fixture (not shown). In this embodiment, the fixture is permanently attached to the CMP system described above in relation to FIG. 1, and the fixture is pivoted out of position from above the CMP pad 404 during normal CMP processing. With this embodiment, the user can simply pivot the fixture into position above the CMP pad 404 and start the automated chemical collection assembly 430. Advantageously, this embodiment allows for a quick transition between ordinary CMP processing and testing the CMP pad cleanliness.

Although the foregoing description of the preferred embodiment of the present invention has shown, described, and pointed out the fundamental novel features of the invention, it will be understood that various omissions, substitutions, and changes in the form of the detail of the apparatus as illustrated as well as the uses thereof, may be made by those skilled in the art, without departing from the spirit of the invention. Consequently, the scope of the invention should not be limited to the foregoing discussions, but should be defined by the appended claims.

What is claimed is:

1. A method of determining the cleanliness of a CMP pad comprising:

positioning a retaining structure on a first surface of the CMP pad so as to define a controlled space;

injecting a controlled volume of solution onto the CMP pad within the controlled space, wherein the solution is selected to dissolve contaminants on the CMP pad;

extracting the solution with the dissolved contaminants from the controlled space adjacent the CMP pad;

sampling the extracted solution to determine the quantity of dissolved contaminants on the CMP pad; and determining, based on the sampling of the extracted solution, whether the CMP pad meets a pre-selected cleanliness threshold.

2. The method of claim 1, wherein determination of whether the CMP pad meets the pre-selected cleanliness threshold is based on ion coupled plasma analysis.

3. The method of claim 1, wherein the solution comprises 1% nitric acid.

4. The method of claim 1, wherein the solution is injected using a pipette.

5. The method of claim 1, wherein the solution is injected using a hollow cylinder with a first end lying adjacent to the retaining structure, wherein the first end comprises a valve which substantially controls the flow of solution into the retaining structure.

6. The method of claim 1, wherein positioning a retaining structure on a first surface of the CMP pad comprises positioning a ring shaped retaining structure on an exposed surface of the CMP pad.

7. The method of claim 1, wherein positioning a retaining structure on a first surface of the CMP pad comprises positioning a retaining structure into a groove of the CMP pad to thereby define the controlled space.

8. The method of claim 7, wherein positioning a retaining structure on a first surface of the CMP pad comprises positioning a retaining structure into the groove such that the retaining structure and the walls of the groove define the controlled space.

9. An assembly for obtaining a sample indicative of the cleanliness of a CMP pad having a first surface, the assembly comprising:

a retaining structure that is positionable adjacent the first surface so as to define an enclosed volume adjacent the first surface of the CMP pad;

a reservoir containing a sampling solution;

a delivery mechanism for delivering the sampling solution to the enclosed volume such that the sampling solution absorbs contaminants on the first surface of the CMP pad;

an extraction mechanism that extracts the sampling solution from the enclosed volume such that the extracted sampling solution contains contaminants of the first surface of the CMP pad so that the sampling solution can be evaluated to determine the cleanliness of the first surface of the CMP pad.

10. The assembly of claim 9, wherein the delivery mechanism comprises a pipette that further defines the reservoir and wherein the extraction mechanism comprises a suction source coupled to the pipette.

11. The assembly of claim 9, wherein the reservoir comprises a hollow cylinder containing a plunger and wherein the delivery mechanism comprises a funnel coupled to a first end of the reservoir such that depression of the plunger delivers sampling solution to the enclosed volume via the funnel and wherein the plunger and reservoir define the extraction mechanism such that retraction of the plunger creates a vacuum source that retracts the sampling solution from the enclosed volume into the reservoir for further sampling.

12. The assembly of claim 9, wherein the retaining structure comprises a continuous wall that defines an inner space such that when the continuous wall is positioned in contact with the first surface of the CMP pad the continuous wall and the first surface of the CMP pad define the enclosed volume.

13. The assembly of claim 12, wherein the retaining structure defines a ring shaped structure.

14. The assembly of claim 9, wherein the retaining structure comprises at least one wall that is positionable with respect to a surface of the CMP pad such that the wall in combination with the CMP pad defines the enclosed volume.

15. The assembly of claim 14, wherein the retaining structure comprises a first and second wall that are sized and spaced from each other so as to be positionable within a groove the CMP pad such that the first and second walls and the walls of the groove of the CMP pad define the enclosed volume.

16. The assembly of claim 9, further comprising an actuator coupled to the retaining structure that positions the retaining structure adjacent the first surface of the CMP pad.

17. The assembly of claim 16, further comprising a controller that provides control signals to the actuator, the delivery mechanism and the extraction mechanism such that positioning of the retaining structure, delivering of the sampling solution and extraction of the sampling solution is automatically controlled by the controller.

18. The assembly of claim 17, wherein the controller initiates operation of the extraction mechanism a preselected period of time after actuation of the delivery mechanism.

19. An assembly for assessing the cleanliness of a CMP pad comprising:

a retaining structure that is adapted to be positioned adjacent a surface of the CMP pad, wherein the retaining structure defines an enclosed volume that retains fluid within the enclosed volume adjacent the surface of the pad; and a pipette that stores a cleaning solution, wherein the cleaning solution in the pipette can be injected onto the surface of the CMP pad within the enclosed volume and wherein the cleaning solution can be extracted from the enclosed volume for subsequent analysis to determine the level of contaminants to thereby ascertain whether the CMP pad is suitable for continued use.

20. The assembly of claim 19, wherein the retaining structure comprises a first surface and a wall extending from the periphery of the first surface wherein the wall defines an aperture which the CMP pad covers during assessment of the CMP pad cleanliness.

21. The assembly of claim 20, wherein the lower aperture is shaped to conform to a pattern of grooves in the CMP pad such that the second end of the retaining structure lies substantially in a groove of the CMP pad and the retaining structure encapsulates a plurality of protrusions located on the CMP pad.

22. The assembly of claim 19, wherein the retaining structure comprises a plurality of walls that are designed to fit inside a groove of the CMP pad and lie adjacent protrusions extending from the CMP pad, wherein the enclosed volume is defined by the walls and the protrusions.

23. A system for evaluating the cleanliness of a surface of a CMP pad, the system comprising:

a delivery system for delivering cleaning solution to the surface of the CMP pad;

a retaining structure that is positionable with respect to the surface of the CMP pad so as to define an area on the surface of the CMP pad into which the delivery system positions the cleaning solution;

a recovery system that recovers cleaning solution from the area on the CMP pad for subsequent analysis; and a controller that sends signals to the delivery system and the recovery system so as to induce delivery and recovery of the cleaning solution.

24. The system of claim 23, wherein the retaining structure comprises a wall that defines an upper aperture at the first end of the wall and a lower aperture at a second end of the wall wherein the CMP pad covers the lower aperture during assessment of the CMP pad cleanliness.

25. The system of claim 24, wherein the lower aperture is shaped to conform to a pattern of grooves in the CMP pad such that the second end of the retaining structure lies substantially in a groove of the CMP pad and the retaining structure encapsulates a plurality of protrusions located on the CMP pad.

26. The system of claim 25, wherein the retaining structure comprises a plurality of walls that are designed to fit inside a groove of the CMP pad and lie adjacent protrusions extending from the CMP pad, wherein the enclosed volume is defined by the walls and the protrusions.

27. The system of claim 23, wherein the delivery system comprises a hollow reservoir and wherein the delivery system further comprises a stem section lying adjacent a first lower end of the reservoir, and wherein the stem section lies adjacent the upper aperture of the retaining structure, and wherein the stem section channels cleaning solution from the reservoir to the retaining structure.

28. The system of claim 23, further comprising an analysis system that analyzes the cleaning solution recovered by the recovery system and provides at least one signal indicative thereof, wherein the controller also receives signals from the analysis system indicative of the cleanliness of the surface of the pad.

* * * * *